(12) United States Patent
Ellingson et al.

(10) Patent No.: US 7,136,158 B2
(45) Date of Patent: Nov. 14, 2006

(54) OPTICAL APPARATUS FOR LASER SCATTERING BY OBJECTS HAVING COMPLEX SHAPES

(75) Inventors: William A. Ellingson, Naperville, IL (US); Robert J. Visher, Downers Grove, IL (US)

(73) Assignee: UChicago Argonne LLC, Chicago, IL (US)

( * ) Notice: Subject to any disclaimer, the term of this patent is extended or adjusted under 35 U.S.C. 154(b) by 113 days.

(21) Appl. No.: 10/865,651

(22) Filed: Jun. 10, 2004

(65) Prior Publication Data

US 2005/0275832 A1    Dec. 15, 2005

(51) Int. Cl.
G01N 21/00 (2006.01)
(52) U.S. Cl. .................................. 356/237.1
(58) Field of Classification Search ...................... None
See application file for complete search history.

(56) References Cited

U.S. PATENT DOCUMENTS

| | | | |
|---|---|---|---|
| 4,765,742 A * | 8/1988 | Davinson .................... 356/624 |
| 5,426,506 A | 6/1995 | Ellingson et al. |
| 5,689,332 A | 11/1997 | Ellingson et al. |
| 5,963,319 A * | 10/1999 | Jarvis et al. ................. 356/301 |
| 5,982,499 A * | 11/1999 | Chichester et al. .......... 356/445 |
| 6,095,982 A * | 8/2000 | Richards-Kortum et al. ............. 600/476 |
| 6,285,449 B1 | 9/2001 | Ellingson et al. |
| 6,577,391 B1 * | 6/2003 | Faupel et al. ................ 356/337 |
| 6,737,649 B1 * | 5/2004 | Webster .................. 250/339.07 |
| 6,859,282 B1 * | 2/2005 | Weber et al. ................ 356/446 |

* cited by examiner

*Primary Examiner*—Michael P. Stafira
(74) *Attorney, Agent, or Firm*—Emrich & Dithmar LLC

(57) ABSTRACT

Apparatus for observing and measuring in realtime surface and subsurface characteristics of objects having complex shapes includes an optical fiber bundle having first and second opposed ends. The first end includes a linear array of fibers, where the ends of adjacent fibers are in contact and are aligned perpendicular to the surface of the object being studied. The second ends of some of the fibers are in the form of a polished ferrule forming a multi-fiber optical waveguide for receiving laser light. The second ends of the remaining fibers are formed into a linear array suitable for direct connection to a detector, such as a linear CMOS-based optical detector. The output data is analyzed using digital signal processing for the detection of anomalies such as cracks, voids, inclusions and other defects.

7 Claims, 4 Drawing Sheets

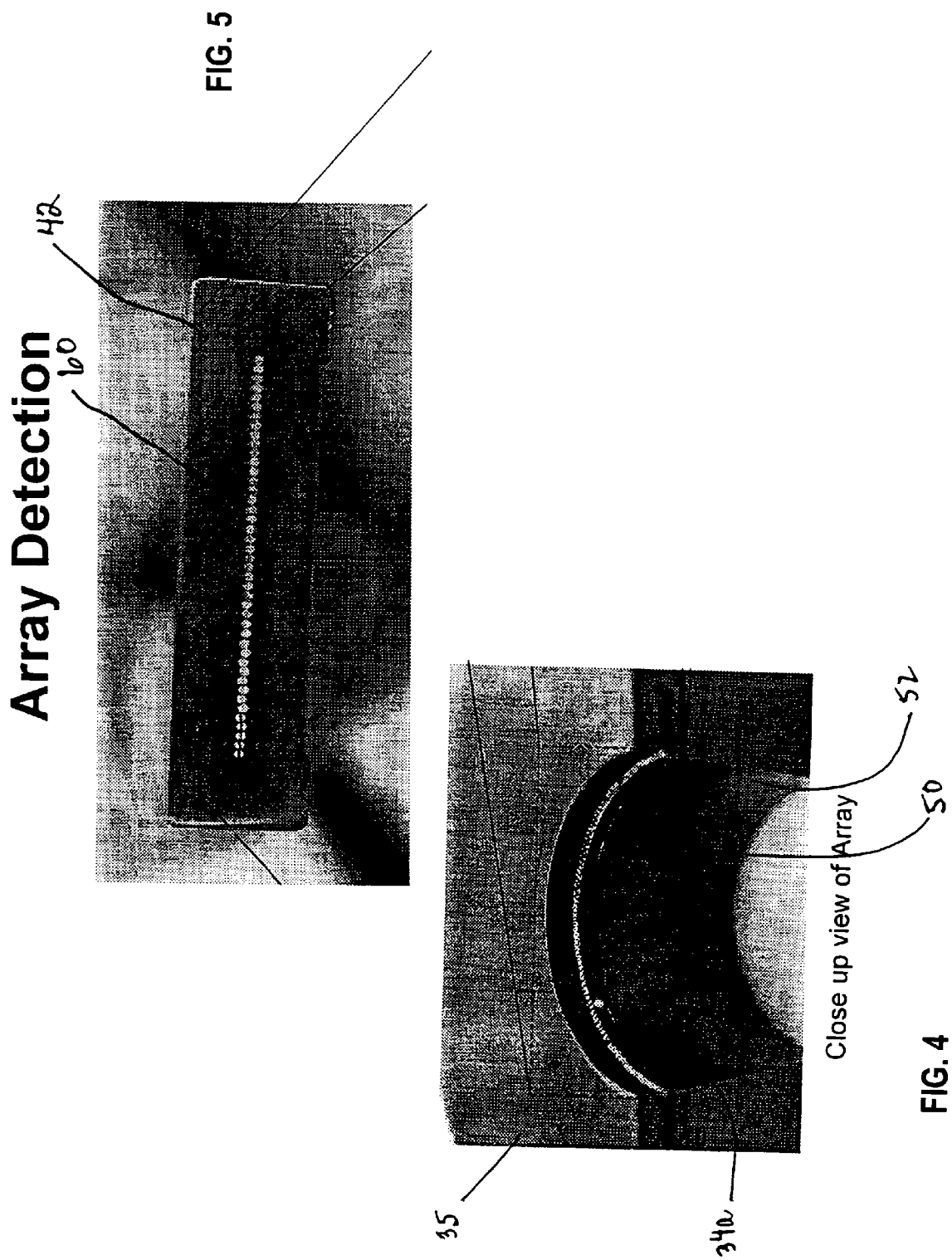

OPTICAL APPARATUS FOR LASER SCATTERING BY OBJECTS HAVING COMPLEX SHAPES

CONTRACTUAL ORIGIN OF THE INVENTION

The United States Government has rights in this invention pursuant to Contract No. W-31-109-ENG-38 between the U.S. Department of Energy (DOE) and The University of Chicago representing Argonne National Laboratory.

FIELD OF THE INVENTION

This invention relates generally to the nondestructive optical analysis of the surface and subsurface characteristics of objects having complex, or irregular, shapes and is particularly directed to the detection and analysis of defects and micro-structural changes in monolithic and composite structural ceramic components and deposited coating having irregular shapes using laser light back scattering and digital signal processing.

BACKGROUND OF THE INVENTION

Because of their mechanical and physical properties, such as higher stiffness, corrosion and wear resistance and greater thermal stability, ceramics such as silicon nitride ($Si_3N_4$) ceramics are considered the materials of choice to replace steels in such applications as contact rolling elements, e.g. bearings, where stiffness and wear resistance play a key role. There is also interest in these types of ceramics for high-temperature turbine bearing components where increased thermal stability is critical. For these types of applications, the most critical portions of the ceramic component, i.e., those with the highest stress during operation, are the surface or near-surface (usually to depth of <200 microns) regions. The most common types of defects found in these critical regions are mechanical in nature, such as cracks, spalls, inclusions, voids, etc., and can be either machining or operation induced.

During machining of ceramics, the material encounters high stresses and temperatures. This can result in the formation of radial, lateral and longitudinal cracks. Usually radial and lateral cracks do not significantly reduce the strength of the ceramic. The longitudinal, also called median, cracks are thought to cause the greatest reduction in strength.

Ceramic components are increasingly being studied for use in gas turbines for rotating bearings, vanes and blades. In bearing applications, the critical regions of a component experiencing the highest stresses are frequently the surface and the near-surface regions to a depth on the order of 200–300 microns. A similar argument can be made for components in bending stress applications.

Some of the most critical defects are thus located on or just beneath the surface and originate when the manufactured part undergoes machining. Any machining induced damage which causes part rejection is to be avoided as early in the manufacturing process as possible to avoid cost-added to rejectable parts. An on-line method for determining the amount of surface and sub-surface damage imparted to a ceramic thus has an economic benefit. Using an on-line detection method, machine tool feed rates and contact pressures can be optimized during machining to obtain the highest material removal rates without adversely affecting the mechanical or tribological properties of the ceramic.

One non-destructive method for detecting and analyzing the defects in ceramics employs polarized laser light directed onto the surface of the ceramic body. A simplified schematic diagram of an optical scattering detection system 10 for use in inspecting ceramic materials is shown in FIG. 1. In this arrangement, a polarized laser beam 14 is directed onto the surface of an object 12 being studied. The incident light is polarized to allow for discrimination between surface and subsurface defects using the material's Brewster angle. A portion of the incident laser beam 14 is directed through the material as a transmitted beam 18 and a portion is reflected as well as scattered from the surface of the object 12 in the form of a surface reflected beam 16. A portion of the incident laser beam 14 also appears as internal scatter 20 within the object 12 being studied and is absorbed by the object. The incident laser beam 14 must be normal to the surface of the object 12 and the detected reflected beam 22 is directed through a polarized object lens 24 and to a first detector 26 as well as to a second detector 28. The first detector 26 detects light reflected from the surface of the object 12, while the second, larger detector 28 detects light scattered by the subsurface portion of the object. Graphically shown in FIG. 1a is the distribution of back-scattered light from the object under investigation, with increased back-scattering occurring in the presence of a defect in the object under investigation. The intensity of the back-scattered light is plotted along the vertical axis, while the spatial distribution of the back-scattered light is plotted along the horizontal axis.

Prior approaches in the area of non-destructive evaluation and characterization of ceramic and ceramic coated objects in a production environment have met with only limited success. For example, because the incident light must be perpendicular to the surface of the object under investigation and because most objects are of an irregular shape, prior approaches involved complex movement of the components under investigation and/or the incident laser beam. Complicated movement of the component under investigation requires a sophisticated displacement arrangement making measurement stability and repeatability more difficult. In addition, prior complicated ceramic component and/or laser beam displacement and positioning systems require an equally complex optical arrangement increasing the time required for detection and analysis of defects rendering these prior approaches impractical for use in on-line production inspection of ceramic components.

The present invention addresses the aforementioned limitations of the prior art by providing optical apparatus for use in detecting and analyzing defects and micro-structural changes in monolithic and composite structural ceramic components as well as in deposited coatings. The optical apparatus if particularly adapted for use with irregularly shaped components and provides highly accurate and repeatable nondestructive evaluation of objects having complex shapes in realtime so as to be particularly effective in an on-line production inspection environment.

OBJECTS AND SUMMARY OF THE INVENTION

Accordingly, it is an object of the present invention to provide realtime detection and analysis of the surface and subsurface characteristics of an object, particularly an object of ceramic composition or having a ceramic surface coating.

It is another object of the present invention to detect defects and micro-structural changes in monolithic and composite structural ceramic components and deposited coatings having complex shapes.

Yet another object of the present invention is to detect and analyze in realtime surface and subsurface anomalies such as cracks, voids, inclusions and other similar defects in objects using scattered laser light, fiber optic arrays, CMOS detectors and digital signal processing.

A further object of the present invention is to detect surface and subsurface defects in an object using light scattered by the object and a fiber optic light delivery and detection arrangement shaped to match the surface of the object which simplifies movement of the object under investigation or the source of light and accommodates objects having highly irregular shapes.

Another object of the present invention is to reduce the required time and improve reproduceability in the non-destructive detection and analysis of surface and subsurface characteristics of objects.

A still further object of the present invention is to simplify the optical arrangement in a laser light scattering detector for analyzing the surface and subsurface characteristics of objects to permit use of the detector in more hostile environments such as encountered in manufacturing, in general, and on a production line, in particular.

This invention contemplates apparatus for detecting and analyzing surface and subsurface characteristics of a body using laser light scattered from the body. The apparatus comprises a first array of light transmitting and receiving optical fibers, wherein the first end of the first array of optical fibers forms a multi-fiber optical waveguide adapted to transmit laser light and the optical fibers on the second end of the first array of optical fibers are disposed adjacent to and aligned generally perpendicular to the surface of the body; a second array of optical fibers having third and fourth opposed ends, wherein the third ends of the second array of optical fibers are disposed adjacent the surface of the body and are aligned generally perpendicular to the surface of the body and are adapted to receive laser light reflected by the body, and wherein the fourth ends of the second array of optical fibers form an optical connector; and a detector coupled to the optical connector for measuring the intensity of laser light reflected from the body representing surface and subsurface characteristics of the body.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 1a is a graphic comparison of the spatial distribution of back-scattered laser light from a ceramic body with and without defects;

FIG. 4 is a partial perspective view of a portion of a fiber optic array disposed in a closely spaced manner from the ceramic object being analyzed by the optical analysis apparatus of the present invention; and FIG. 5 is an end-on view of a fiber optic array detection connector for use in the optical analysis apparatus of the present invention.

DETAILED DESCRIPTION OF THE PREFERRED EMBODIMENTS

Figure 1:
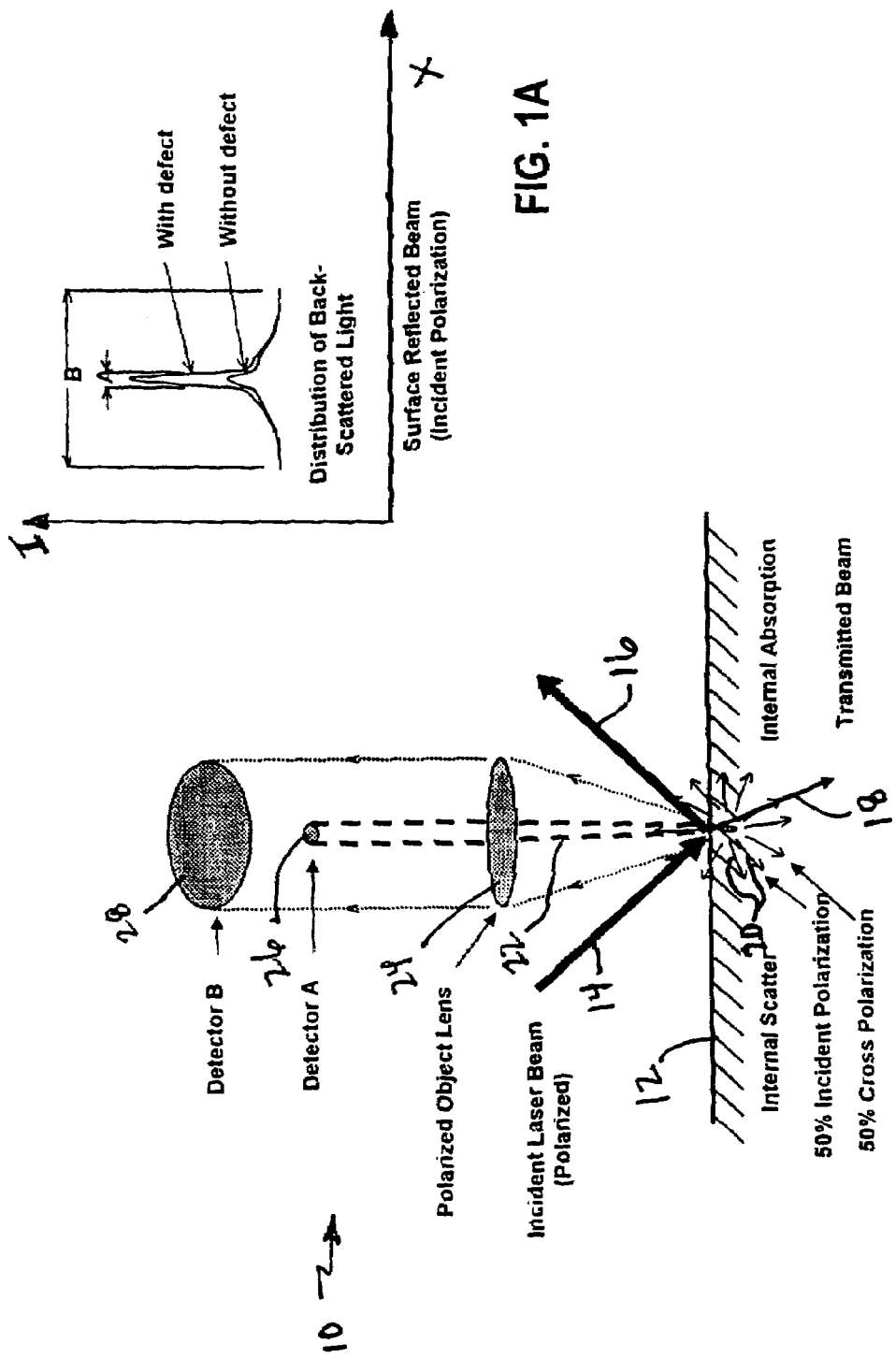
FIG. 1 is a simplified schematic diagram of an arrangement for detecting and analyzing surface and subsurface defects in a ceramic object or an object having a ceramic surface coating as employed in the prior art.
Figure 2:
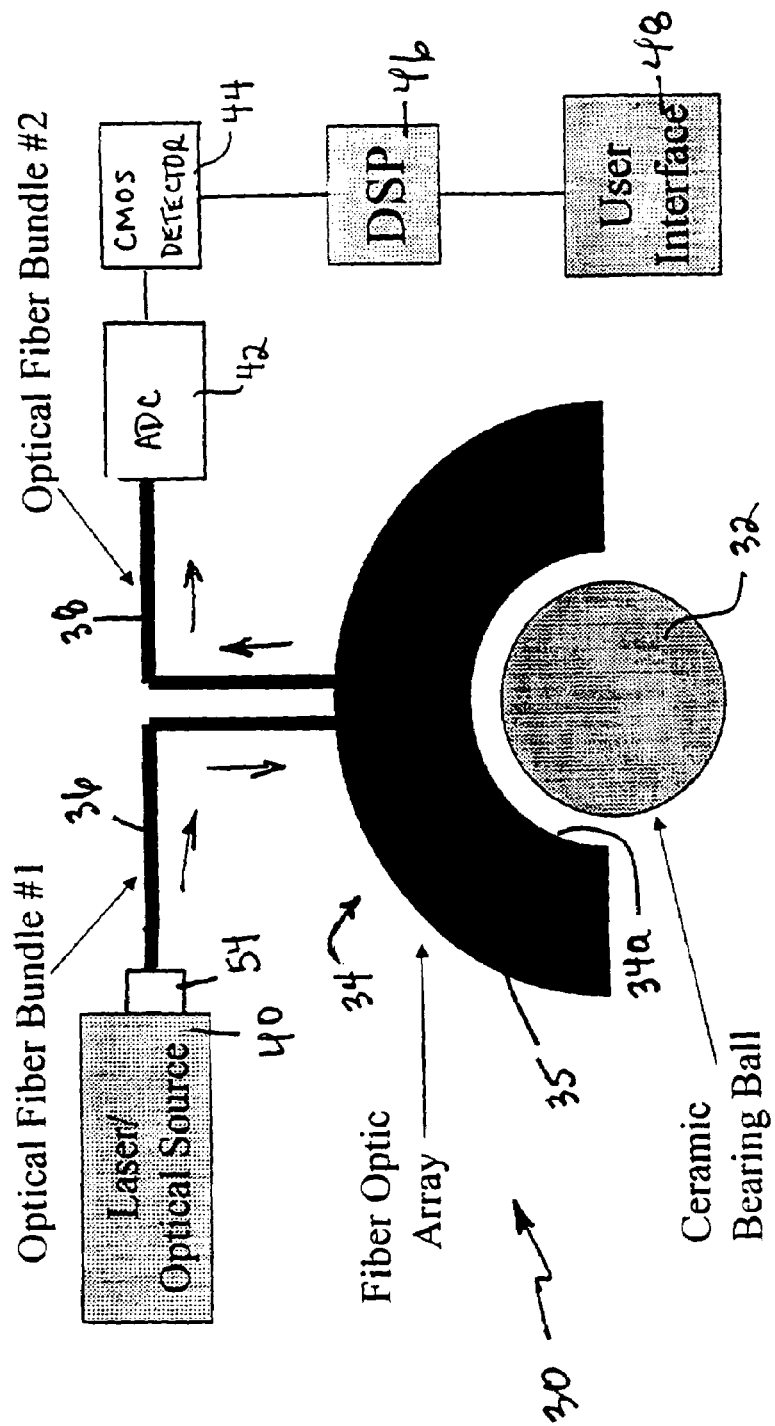
FIG. 2 is a simplified combined schematic and block diagram of an optical analysis apparatus in accordance with the present invention for detecting and analyzing surface and subsurface defects in a ceramic object or an object having a ceramic surface coating.
Figure 3:
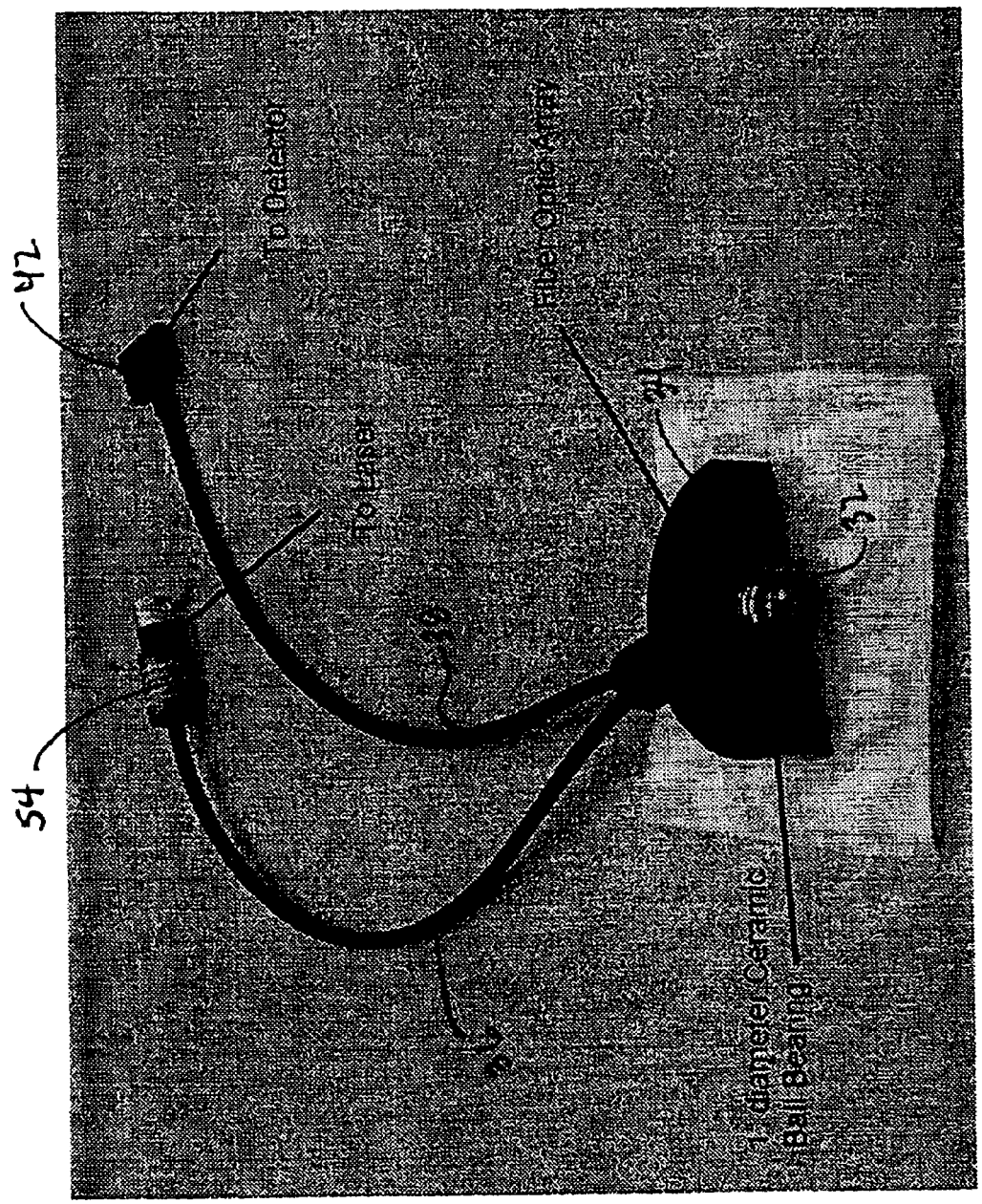
FIG. 3 is a perspective view of the sensor portion of the optical analysis apparatus of the present invention.

Referring to FIG. 2, there is shown a simplified combined schematic and block diagram of an optical analysis apparatus 30 in accordance with the principles of the present invention. A perspective view of the optical portion of the optical analysis apparatus 30 of the present invention is shown in FIG. 3. Optical analysis apparatus 30 is shown analyzing the surface and subsurface of a complex shaped object in the form of a ceramic bearing ball 32. Optical analysis apparatus 30 includes a fiber optic array 34 having a housing 35 with first surface 34a contoured to conform to an outer surface of the ceramic bearing ball 32. To conform to a portion of the outer surface of the ceramic bearing ball 32, the fiber optic array's housing 35 has a generally semi-circular configuration. Attached to and extending into the fiber optic array's housing 35 are first and second optical fiber bundles 36 and 38. The ends of the optical fibers in the first and second optical fiber bundles 36 and 38 are disposed on the inner surface 34a of the fiber optic array's housing 35.

The ends of each of the optical fibers within the first and second optical fiber bundles 36, 38 within housing 35 are oriented generally perpendicular to the portion of the outer surface of the ceramic bearing ball 32 closest to the optical fiber. The fiber optic array's housing 35 is comprised of material capable of maintaining each of the optical fibers disposed within the fiber optic array in fixed position therein. In one embodiment, housing 34 is comprised of a molded plastic within which are embedded the optical fibers extending from the first and second optical fiber bundles 36 and 38. The fiber optic array 34 may be comprised of a conformable, or pliable, material so that its shape, or configuration, can be changed to match the shape of the outer surface of the object being analyzed. Thus, the fiber optic array's housing 35 can be adapted for use in detecting and analyzing the surface and subsurface characteristics of various objects having virtually any outer shape and form. However, the conformability of housing 35 should be limited so as not to allow the flexibility limits of the optical fibers within the housing to be exceeded resulting in breaking of the optical fibers.

The individual optical fibers extending from the first optical fiber bundle 36 and the second optical fiber bundle 38 and into the fiber optic array's housing 35 are placed in contact with one another. In addition, the ends of the first and second optical fiber bundles 36, 38 within housing 35 are arranged in an alternating manner. With a first end of the first optical fiber bundle 36 disposed in housing 35, a second, opposed end of the first optical fiber bundle is optically coupled to an optical signal source, i.e., a laser, 40. The end of the first optical fiber bundle 36 disposed adjacent laser/optical source 40 is shaped in the form of a ferrule, or ring, 54 for the purpose of strengthening and preventing separation of the ends of the adjacent optical fibers. The ferrule-configured ends of the optical fibers within the first optical fiber bundle 36 disposed adjacent the laser/optical source 40 form a multi-fiber optical waveguide for receiving the laser light output of the laser/optical source.

Referring to FIG. 4, there is shown a perspective view of the inner portion of the fiber optic array's housing 35 within which the optical fibers of the first and second optical fiber bundles 36, 38 are disposed. As shown in the figure, the ends 52 of the optical fibers disposed within the inner, concave portion 34a of the fiber optic array's housing 35 are disposed in a linear array. In a preferred embodiment, the respective ends of the optical fibers in the first and second optical fiber bundles 36, 38 are disposed within a groove, or notch, 50 within the concave portion 34a of housing 50 and are arranged in an alternating manner in the optical fiber end array. The second, opposed ends of the optical fibers in the second optical fiber bundle 38 are arranged in a linear array 60 within an array detection connector 42 which is adapted for coupling to a complementary metal oxide (CMOS) detector 44 as shown in FIGS. 2 and 5.

Thus, the fiber optic system includes a special fiber optic bundle having one end formed into a first linear array and disposed within the fiber optic array's housing 35 and two opposed ends formed from the first and second optical fiber bundles 36, 38 with special features. One portion of the opposed end of the fiber optic array is formed into the aforementioned ferrule 54 to provide a multi-fiber optical waveguide for receiving laser light from the laser/optical source 40. Another portion of the opposed end of fiber optic array is formed into a linear optical fiber end array 60 within the array detection connector 42 for coupling to the CMOS detector 44. The laser light is focused on the end of the ferrule 54 adjacent the laser/optical source 40 so that the intensity of the laser light is evenly distributed over the entire ferrule and uniformly transmitted to each of the optical fibers. Light from the laser/optical source 40 then passes through the first optical fiber bundle 36 and is directed onto the surface of the ceramic bearing ball 32 as the light exists the fiber optic array's housing 35. The incident laser light is reflected from the surface and subsurface of the ceramic bearing ball 32 and is received by the ends of the optical fibers within the second optical fiber bundle 38 which are also disposed within the concave inner portion 34a of the fiber optic array's housing 35. The reflected light then passes through the second optical fiber bundle 38 to the CMOS detector 44 via the linear optical fiber end array 60 disposed within the array detection connector 42.

The CMOS detector 44 measures the intensity of the back-scattered light collected by the fiber optic array 34. CMOS detector 44 offers the following advantages over existing charged coupled device (CCD) detectors: reduced cost; integrated support electronics, i.e., amplification, conversion and timing; lower power consumption; and no requirement for external cooling. In addition, the use of CMOS detector 44 allows each pixel of the back scattered laser light to be accessed independently. The output of the CMOS detector 44 is provided to a digital signal processor 46 for processing the optical data in realtime. A user interface 48 connected to the digital signal processor 46 allows the user to control data acquisition, sample the motion of the object being tested, i.e., the ceramic bearing ball 32, and to provide feedback relating to the detected surface and subsurface characteristics of the object being evaluated. User interface 48 is in the form of a personal computer (PC) or a go/no go logic device such as used in a high speed production environment.

While particular embodiments of the present invention have been shown and described, it will be obvious to those skilled in the relevant arts that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The invention claimed is:

1. Apparatus for detecting and analyzing surface and subsurface characteristics of a body using laser light scattered from the body, said apparatus comprising:

a first array of light transmitting optical fibers having first and second opposed ends, wherein the first end of said first array of optical fibers are polished and arranged in the shape of a ferrule for forming a multi-fiber optical waveguide adapted to transmit laser light and the optical fibers on the second end of said first array of optical fibers are disposed adjacent to and aligned generally perpendicular to the surface of the body;

a second array of light transmitting optical fibers having third and fourth opposed ends, wherein the third ends of said second array of optical fibers are disposed adjacent the surface of the body and are aligned generally perpendicular to the surface of the body and are adapted to receive laser light reflected by the body, and wherein the fourth ends of said second array of optical fibers form an optical connector;

a housing coupled to and enclosing the second ends of said first array of optical fibers and the third ends of said second array of optical fibers for connecting the optical fiber ends together in a fixed configuration and for maintaining the optical fiber ends in fixed position relative to the surface of the body during detection and analysis of surface and subsurface characteristics of the body, wherein said housing is pliable so as to be conformable to the shape of the surface of the body for maintaining the second ends of said first array of optical fibers and the third ends of said second array of optical fibers in conformance with the shape of the surface of the body, and wherein the second ends of said first array of optical fibers and the third ends of said second array of optical fibers are in linear alignment in said housing and are equidistant from the surface of the body; and a CMOS detector coupled to said optical connector for measuring the intensity of laser light reflected from the body representing surface and subsurface characteristics of the body.

2. The apparatus of claim 1 wherein the second ends of said first array of optical fibers and the third ends of said second array of optical fibers are arranged in a closely spaced, alternating manner adjacent the surface of the body.

3. The apparatus of claim 1 wherein said housing is comprised of a molded plastic.

4. The apparatus of claim 1 wherein the laser light is focused on an end of said ferrule so that the intensity of the laser light is evenly distributed over the entire ferrule.

5. The apparatus of claim 1 wherein the second ends of said first array of optical fibers and the third ends of second array of optical fibers are arranged in a first linear array.

6. The apparatus of claim 5 wherein the fourth ends of the second array of optical fibers are arranged in a second linear array.

7. The apparatus of claim 1 further comprising a digital signal processor coupled to said detector for processing signals representing the laser light reflected from the body.

* * * * *

UNITED STATES PATENT AND TRADEMARK OFFICE
CERTIFICATE OF CORRECTION

| | | |
|---|---|---|
| PATENT NO. | : 7,136,158 B2 | Page 1 of 1 |
| APPLICATION NO. | : 10/865651 | |
| DATED | : November 14, 2006 | |
| INVENTOR(S) | : William A. Ellingson and Robert J. Visher | |

It is certified that error appears in the above-identified patent and that said Letters Patent is hereby corrected as shown below:

Column 1, line 19, delete "coating" and insert --coatings--.
Column 2, line 52, delete "if" and insert --is--.
Column 5, line 37, delete "exists" and insert --exits--.

Signed and Sealed this

Thirteenth Day of February, 2007

JON W. DUDAS
*Director of the United States Patent and Trademark Office*